United States Patent [19]

Sato et al.

[11] Patent Number: 4,770,170

[45] Date of Patent: Sep. 13, 1988

[54] CUFF PRESSURE REGULATOR FOR ENDOTRACHEAL-TUBE CUFF

[75] Inventors: Toru Sato; Toshihisa Hasegawa, both of Yonago, Japan

[73] Assignee: Tottori University, Tottori, Japan

[21] Appl. No.: 879,437

[22] Filed: Jun. 27, 1986

[30] Foreign Application Priority Data

Jul. 3, 1985 [JP] Japan ............................... 60-144435

[51] Int. Cl.⁴ ............................................ A61M 16/00

[52] U.S. Cl. ........................... 128/207.15; 128/205.24

[58] Field of Search ...................... 128/207.14, 207.15, 128/207.16, 205.24; 604/96–99

[56] References Cited

U.S. PATENT DOCUMENTS

| | | | |
|---|---|---|---|
| 3,931,822 | 1/1976 | Mavici | 128/207.15 |
| 3,985,141 | 10/1976 | Stanley et al. | 128/207.15 |
| 4,119,101 | 10/1978 | Igich | 128/207.15 |
| 4,159,722 | 7/1979 | Walker | 128/207.15 |
| 4,178,938 | 12/1979 | Au | 128/207.15 |
| 4,178,940 | 12/1979 | Au | 128/207.15 |
| 4,285,340 | 8/1981 | Gezari et al. | 128/207.15 |
| 4,471,775 | 9/1984 | Clair et al. | 128/207.15 |
| 4,501,273 | 2/1985 | McGinnis | 128/207.15 |
| 4,526,196 | 7/1985 | Pistillo | 128/207.15 |
| 4,583,917 | 4/1986 | Shah | 128/207.15 |

FOREIGN PATENT DOCUMENTS 7742 2/1955 Japan .

OTHER PUBLICATIONS

Japanese Journal of Medical Instrumentation, vol. 51, Suppl. 1981, pp. 190–192, "72. Apparatus for Controlling Cuff Pressure during Nitrous Oxide–Oxygen Anesthesia."

Sapporo Ishi, (Medical Journal), 50(5), 1981, pp. 363–371, "Changes in Intra– and Lateral–Cuff Pressure During Nitrous Oxide Anesthesia and Clinical Evaluation of a New Cuff Pressure Regulator".

*Primary Examiner*—Edward M. Coven
*Assistant Examiner*—K. M. Reichle
*Attorney, Agent, or Firm*—Spencer & Frank

[57] ABSTRACT

A cuff regulator for an endotracheal-tube cuff comprising a first chamber connected to a pressurized gas supply source, and a second chamber connected to the first chamber through a pressure regulating valve and having an opening connected to a cuff of the cuffed endotracheal-tube. An orifice open to the external environment is provided in a part of a gas conduit between the second chamber and the cuff. A third chamber is also provided having the same pressure as that of the environment in which the cuff is existent. A valve driving apparatus drives the pressure regulating valve in response to the pressure difference between the third chamber and the second chamber, and a pressure setting device sets a desired cuff pressure at which opening and closing operations of the pressure regulating valve are actuated. With such construction, gas having a pressure higher than the desired cuff pressure is supplied from the pressurized gas supply source to the first chamber, and the cuff pressure is maintained at the desired cuff pressure set by the pressure setting device while the gas is slowly discharged toward the external environment through the orifice.

5 Claims, 2 Drawing Sheets

21 20 22 24 26 25 23 13 19 3 1 10 11 12 4 9 8 5 14 15 18 16 17 7 2 6 GAS SUPPLY 21
20
22
24
26
25
1
10
12
23
11
4
13
3
9
19
8
5
14
GAS
SUPPLY
15
6
18
16
17
7
2

CUFF PRESSURE REGULATOR FOR ENDOTRACHEAL-TUBE CUFF

BACKGROUND OF THE INVENTION

1. Field of the Invention

This invention relates to a cuff pressure regulator for an endotracheal-tube cuff.

2. Related Art Statement

Heretofore, in artificial ventilation under general anesthesia or through a tracheotomy, there has been used a cuffed endotracheal-tube for intubation and tracheotomy to prevent a leakage of anesthetic gas, oxygen or air toward the outside and to prevent the inflowing of vomitus from the esophagus into the trachea. In the cuffed endotracheal-tube, if the cuff is brought into contact with the inner wall of the trachea under high pressure, normal blood flow in the mucosa is disturbed due to excess pressure for capillary vessels at the contact portion, and there occurs a dysfunction of said tunica mucosa (ciliary epithelium) so that, in an extreme case, such contact portion becomes necrotic.

Contrary to this, if the cuff is brought into contact with the inner wall of the trachea under too low a pressure, the artificial respiration can be inhibited due to a leakage of anesthetic gas, oxygen or air, and the vomitus is allowed to flow into the lungs from the esophagus. Therefore, in the cuffed endotracheal-tube, it is necessary to maintain the cuff contact pressure on the inner wall of the trachea at a suitable level such that neither gas supplied from an anesthesia machine or a respirator leaks nor blood flow in the capillaries at the contact portion is disturbed.

In the Japanese Utility Model Publication No. 7,742/85, there has been proposed an apparatus for controlling the cuff pressure wherein, on the basis of Pascal theory, pressure in a small vessel connected to the cuff, i.e., the inner pressure of the cuff, can be maintained at a desired level by changing the weight or the amount of liquid in a bottle on a bellows or a cylinder arranged movably up and down in the vessel.

Further, in Japanese Journal of Medical Instrumentation vol. 51, Suppl., 1981, pp. 190–192 "72. Apparatus for controlling cuff pressure during nitrous oxide-oxygen anesthesia" and a society magazine of "Sapporo Ishi" (Medical Journal) 50(5). 1981. pp. 363–371 titled "Changes in Intra- and Lateral-Cuff Pressure during Nitrous Oxide Anesthesia and Clinical Evaluation of a New Cuff Pressure Regulator", there has been proposed a cuff pressure regulator for keeping the cuff inner pressure at a constant level by introducing air through a filter by operation of a diaphragm pump, supplying the thus introduced compressed air to a Y-connector through a pressure-reducing valve under a predetermined pressure higher than the cuff maximum pressure, connecting one output end of the Y-connector to the cuff, connecting the other output end of the Y-connector to the ambient through an adjustable orifice and controlling the discharge amount of surplus air by said orifice.

However, in the former cuff pressure regulator mentioned above, since the desired cuff pressure is achieved by changing the weight of or the amount of liquid in a bottle arranged on the bellows or the cylinder, it is necessary to select one among many weights, each having a different weight, or to adjust the amount of said liquid to obtain a desired weight. Therefore, there is a drawback in that it is very cumbersome to achieve such adjustment. Moreover, in order to have the weight exactly correspond to the cuff pressure when using the bellows it is necessary to make the dynamic resistance of the bellow extremely small and to manufacture it uniformly, and when using the cylinder it is necessary to move the cylinder airtightly with no resistance against the vessel wall. Therefore, in both cases, there is a drawback in that it is very difficult to manufacture the cuff pressure regulator in an easily operable and inexpensive manner. Further, since the cuff pressure is obtained by the weight, the cuff pressure can not be achieved effectively if the cuff pressure regulator falls or is laid down. In addition, in an extreme case of such falling down or being laid down, the cuff pressure is abruptly decreased and becomes even negative, so that the patient during operation under anesthesia may fall into a dangerous condition. Still it is impossible to correct such disturbed situation from the outside of an isolated space such as a hyperbaric chamber.

In the latter cuff pressure regulator mentioned above, since the cuff pressure is adjusted by controlling the discharge of the surplus air (having a predetermined pressure set fixedly above the cuff maximum pressure) through an adjustable orifice toward the external environment by using the adjustable orifice, there is a drawback that it is very difficult to achieve a fine adjustment of the cuff pressure. Moreover, since the pressurized air is suplied to the cuff through the pressure-reducing valve by operating the diaphragm pump by means of an electric motor, the cuff pressure is pulsating due to the motion of said diaphragm pump, and the cuff pressure is abruptly decreased to the atmospheric pressure if the power supply is accidentally interrupted, so that the patients can be endangered. Further, since said pump pressure usually becomes too low and also because it is necessary to prohibit an installation of an electric motor etc. in a hyperbaric oxygen chamber for the sake of safety, there occurs a drawback in that a cuff pressure regulator of this type can not be used for hyperbaric oxygen treatment.

When a cuff filled with a gas such as oxygen is used in a hyper- (or hypo-) baric chamber and the like, the cuff volume increases (or decreases) corresponding to a decrease (or an increase) of relative cuff pressure due to an abrupt change of the environmental pressure. Therefore, it is necessary to maintain the cuff contact pressure against the trachea wall without variation of the cuff volume. To this end, water is widely used instead of gas for this purpose. However, since it is almost impossible to adjust precisely the cuff contact pressure against the trachea inner wall when water or liquid is used to inflate the cuff instead of gas, there likely occur serious complications because of no elasticity in the cuff.

SUMMARY OF THE INVENTION

The present invention has for its object to eliminate the drawbacks mentioned above and to provide a cuff pressure regulator for an endotracheal-tube cuff wherein the cuff pressure can be easily set at a desired level and the thus set cuff pressure can be automatically and securely maintained during nitrous oxide anesthesia and even if the environmental pressure is abruptly varied such as in an airplane or a hyperbaric (or hypobaric) chamber. Further, another object of the invention is to provide a cuff pressure regulator which can be manufactured, supplied and safely operated in an easy and inexpensive manner and which can function effectively even if it is laid down or falls down and the gas power source is suddenly and accidentally cut off.

According to the invention, a cuff pressure regulator for an endotracheal-tube cuff for controlling said cuff pressure against a trachea inner wall, comprises a first chamber connected to a pressurized gas supply source; a second chamber connected to said first chamber through a pressure regulating valve and having an opening connected to a cuff of said cuffed endotracheal-tube; an orifice open to the external environment being arranged in a part of a gas conduit between said second chamber and said cuff; a third chamber having the same pressure as that of the environment in which said cuff is existent; a valve driving means for driving said pressure regulating valve in response to the pressure difference between said third chamber and said second chamber; and a pressure setting means for setting a desired cuff pressure at which opening and closing operations of said pressure regulating valve are actuated; whereby gas having a pressure higher than the desired cuff pressure is supplied from said pressurized gas supply source to said first chamber and the cuff pressure is maintained at the desired cuff pressure set by said pressure setting means while the gas is slowly discharged toward the external environment through said orifice.

DESCRIPTION OF THE PREFERRED EMBODIMENTS

Figure 1:
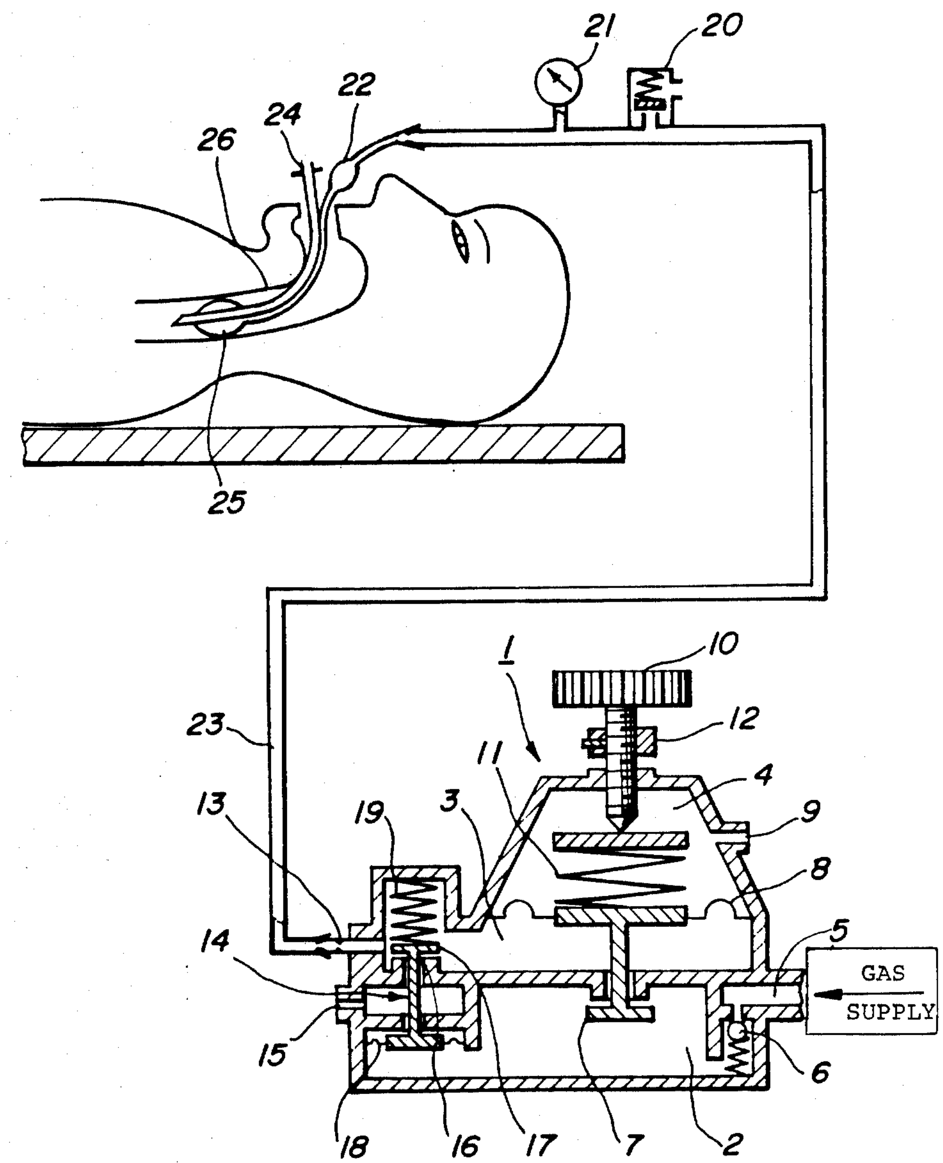
FIG. 1 is a schematic view showing one embodiment of the cuff pressure regulator according to the invention.

FIG. 1 is a schematic view showing one embodiment of a cuff pressure regulator according to the invention. A cuff pressure regulator 1 comprises a first chamber 2, a second chamber 3 and a third chamber 4. In the first chamber 2, a connection opening 5 is provided for connecting the cuff pressure regulator 1 to a pressure supply source, and a one-way valve 6 for preventing a back flow of gas from the first chamber 2 toward the pressure supply source when it becomes off or low, is arranged at a connection portion.

The first chamber 2 and the second chamber 3 are are connected through a pressure regulating valve 7, and the second chamber 3 and the third chamber 4 are partitioned and separated from each other by a diaphragm 8. Moreover, the diaphragm 8 is connected to the pressure regulating valve 7 by a rod, and then the pressure regulating valve 7 is actuated in response to the pressure difference between the second chamber 3 and the third chamber 4. An opening 9 is provided in the third chamber 4 to make the pressure of the third chamber 4 identical with the environmental pressure in which the cuff of a cuffed endotracheal-tube is existent. Further, a handle 10 with a screw threaded portion for controlling pressure is arranged in the third chamber 4. By rotating (or operating) the handle 10, the diaphragm 8 is pressed more (or less) through a spring 11 so as to open (or close) the pressure regulating valve 7 at a desired cuff pressure. Moreover, the handle 10 comprises a stopper 12, whereby a cuff pressure in excess of the permissible pressure of the trachea inner wall is prevented.

An opening 13 with a constrictor is connected to the second chamber 3, and an orifice 15 is also provided for venting the second chamber 3 to the outside through a valve mechanism 14. The valve mechanism 14 comprises a valve 17 arranged for closing an opening 16 connected to the orifice 15, a diaphragm 18 arranged in the first chamber 2 and connected to the valve 17, and a spring 19 arranged for pressing the valve 17 into the opening 16 so as to close the opening 16. In this construction, when the pressure of the first chamber 2, i.e. that of a gas supplied from the pressure supply source is lower than a predetermined value, i.e. the maximum cuff pressure adjustable by the handle 10, the opening 16 is closed by the valve 17 so as not to leak the gas through the orifice 15.

In this embodiment, the opening 13 with the constrictor arranged in the second chamber 3 is connected to a cuff 25 of a cuffed endotracheal-tube 24 by means of a tube 23 having a small inner diameter through a safety valve 20, a pressure gauge 21 and a pilot balloon 22. Further, the connection opening 5 of the first chamber 2 is connected to the pressure supply source for supplying gas having a pressure higher than the maximum cuff pressure, which is adjustable by the handle 10, into the first chamber 2.

In this construction mentioned above, when gas having a pressure higher than the maximum cuff pressure is effectively supplied into the first chamber 2 from the pressure supply source, the valve 17 is maintained in the open sate. Moreover, the pressure regulating valve 7 is opened when the pressure in the second chamber 3 is lower than the cuff pressure set by the handle 10, and is closed when the cuff pressure reaches a predetermined value by means of the movement of the diaphragm 8. Therefore, since the pressure in the second chamber 3 is maintained at a desired cuff pressure set by the handle 10 while the gas is discharged toward the outside through the orifice 15, the cuff 25 is brought into adequate contact with the inner wall of a trachea 26 always under a constant contact pressure corresponding to the desired cuff pressure. Further, since the pressure applied to the diaphragm 18 is lower when the pressure in the first chamber 2 becomes lower than the maximum cuff pressure, the valve 17 closes the opening 16 by the force of the spring 19. In this case, gas discharge from the orifice 15 is prevented, and the gas in the first chamber 2 is prevented from flowing backward into the pressure supply source by the one-way valve 6. Therefore, it is possible to maintain the cuff pressure always at the desired pressure set by the handle 10.

In the construction mentioned above, it should be noted that the constrictor in the opening 13 functions to supply gas having a desired pressure level to the cuff 25 and further functions to decrease the gas discharge amount and thus the noise of the gas discharge, in case the connection portion of the tube 23 should be removed (or come off) or the gas should be discharged from the safety valve 20 accidentally.

In the embodiment mentioned above, the cuff pressure is not adjusted by changing the weight of various weights as previously mentioned, but is adjusted by pressing the diaphragm 8 by means of the spring 11 and the handle 10 for controlling the pressure and by driving the pressure regulating valve 7 by means of the diaphragm 8 corresponding to the pressure difference between the second chamber 3 and the third chamber 4. Therefore, it is possible to set the desired cuff pressure in an easy and continuous manner and to maintain the thus set pressure accurately and automatically even if the apparatus falls or is laid down, and further the apparatus according to the invention can be manufactured in an easy and inexpensive manner. Moreover, since the stopper 12 is arranged an the handle 10 for controlling the pressure, it is possible to effectively prevent a situation wherein the cuff pressure is set in excess of the permissible pressure of the tracheal inner wall. Further, since the safety valve 20 and the pressure gauge 21 are arranged in a cuff pressure conduit, the cuff pressure can be always detected and monitored by the pressure gauge 21, and it is possible to prevent a situation arising in which the cuff pressure is set in excess of the permissible pressure of the tracheal inner wall even when the safety valve 20 is actuated in an emergency. Moreover, since the gas in the second chamber 3 is discharged from the orifice 15 through the valve mechanism 14, it is possible to maintain the desired cuff pressure even if there occurs variations of the cuff pressure due to diffusion of anesthetic gas into the cuff 25 through the cuff wall, a temperature change, leaking of gas from the cuff 25 and a change in relaxation or strain of the trachea 26. In addition, it is possible to prevent an increase of relative pressure of the cuff with respect to the environment due to an abrupt decrease of the environmental pressure and to prevent an increase of pressure due to a leakage of a small amount of gas through the pressure regulating valve 7. Further, it is possible to change the cuff pressure to a lower level in a rapid manner.

Figure 2:
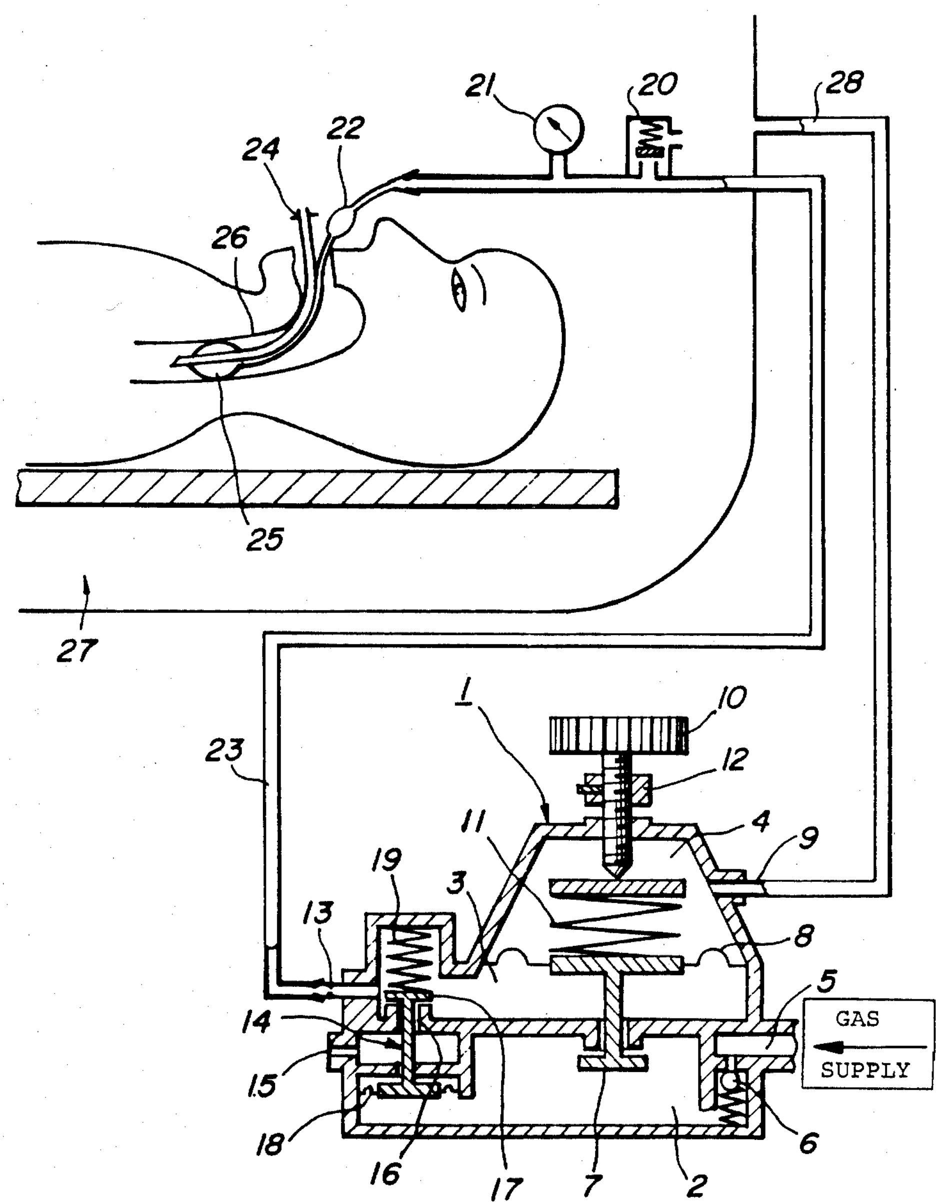
FIG. 2 is a schematic view illustrating another embodiment of the cuff pressure regulator according to the invention.

Further, in this embodiment, the opening 9 is formed in the third chamber 4 to make the pressure of the third chamber 4 identical with the environmental pressure in which the cuff 25 is existent. That is, the environmental pressure which surrounds cuff 25 is the same as the pressure at opening 9 in the third chamber 4 and at the open end of cuffed endotracheal-tube 24. Therefore, as shown in FIG. 2, when a treatment etc. is performed in hyperbaric or hypobaric chamber 27, it is possible to set the cuff pressure arbitrarily from the outside by connecting the hyperbaric or hypobaric chamber 27 to the opening 9 through a pilot tube 28 while the cuff pressure regulator 1 is arranged outside the hyperbaric or hypobaric chamber 27.

The present invention is not limited to the embodiments mentioned above, but various modifications are possible. For example, in the embodiment mentioned above, the pressure regulating valve 7 is driven by the diaphragm 8, but it is possible to construct the pressure regulating valve 7 by a piston instead of the diaphragm. Moreover, when the cuff pressure regulator 1 and the cuff 25 are used under the same environmental pressure, the safety valve 20 and the pressure gauge 21 may be arranged in the cuff pressure regulator 1. Further, as shown in FIG. 2, when the cuff pressure regulator 1 and the cuff 25 are used under different environmental pressures respectively, the pressure in the third chamber 4 of the cuff pressure regulator 1 may be set at the same pressure as that of the environment of the cuff 25 by controlling it by means of a pneumatic source. Moreover, since no electricity is used in the cuff pressure regulator 1, the cuff pressure regulator 1 may be safely used in the hyperbaric or hypobaric oxygen chamber. In this case, there should no problem when the cuff pressure set before the beginning of such treatment is not necessarily changed during the treatment. However, when it is necessary to change the cuff pressure during the treatment, the cuff pressure can be adjusted arbitrarily in the same manner mentioned above by arranging a rotation shaft airtightly through a wall of the hyperbaric or hypobaric chamber and by rotating the handle 10 by means of the rotation shaft. Under such a construction, it is not necessary to have an operator for controlling the cuff pressure, and thus it is possible to use the cuff pressure regulator even in a small hyperbaric or hypobaric chamber in which only a single patient can be treated. Furthermore, in the embodiment mentioned above, the orifice 15 is connected to the second chamber 3, but the orifice 15 may be located at any portions in the gas conduit from the second chamber 3 to the cuff 25. Moreover, in the embodiment mentioned above, the one-way valve 6 and the valve mechanism 14 are provided, but they may be eliminated if the pressure of the gas to be supplied from the pressure supply source is securely maintained.

As mentioned above in detail, according to the invention, it is possible to set the desired cuff pressure in an easy and continuous manner and to maintain the thus set pressure accurately and automatically even if the apparatus is laid down, and further such cuff pressure regulators can be manufactured in an easy and inexpensive manner.

What is claimed is:

1. A cuff pressure regulator for controlling the pressure applied by the cuff of an endotracheal tube to the inner wall of the trachea, comprising a first chamber including means for the connection thereof to a pressurized gas supply source;

a second chamber adapted to be connected to the cuff of the endotracheal tube, said second chamber having an orifice therein for venting said second chamber to the outisde of said regulator;

a third chamber, said third chamber having means for maintaining the pressure therein at the same pressure as that surrounding said cuff;

pressure regulating valve means interposed between said first and second chambers for controlling the flow of gas therebetween;

valve driving means separating said second and third chambers and being connected to said pressure regulating valve means, said valve driving means displacing said pressure regulating valve means in response to a pressure difference between said second and third chambers, said pressure regulating valve means being opened by said valve driving means when the pressure in said second chamber is lower than a predetermined cuff pressure and closed when the pressure in said second chamber reaches said predetermined pressure; and pressure setting means connected to said valve driving means for setting said predetermined cuff pressure at which opening and closing of said pressure regulating valve means is initiated, whereby gas having a pressure higher than said predetermined cuff pressure is supplied from the pressurized gas supply source to said first chamber; and flow controlling valve means for controlling the flow of gas through the orifice in said second chamber, said means allowing the gas to slowly discharge through said orifice when the cuff pressure is being maintained at said predetermined cuff pressure and preventing discharge of gas through said orifice when the gas pressure in said first chamber falls below said predetermined cuff pressure.

2. A cuff pressure regulator according to claim 1, which further comprises a one-way valve interposed between said first chamber and the pressurized gas supply source, said one-way valve preventing a back flow of gas from said first chamber to the pressurized gas supply source.

3. A cuff pressure regulator according to claim 1 wherein said flow controlling valve means comprises a valve for controlling the flow of gas through said orifice, a diaphragm mounted in said first chamber and connected to said valve, and a spring means exerting a pressure on said valve to prevent the flow of gas from said second chamber to said orifice when the pressure in said first chamber falls below said predetermined value.

4. A cuff pressure regulator according to claim 1 wherein said second chamber is adapted to be connected to said cuff by a conduit having a constrictor therein, said constrictor reducing the amount of gas discharged and the noise of said discharge in the event said conduit should become disconnected during operation of said regulator.

5. A cuff pressure regulator according to claim 4 which further comprises a safety valve located in said conduit.

* * * * *